(12) United States Patent
Godfrey et al.

(10) Patent No.: US 6,839,604 B2
(45) Date of Patent: Jan. 4, 2005

(54) COMPLIANCE TRACKING METHOD

(75) Inventors: James William Godfrey, Ware (GB); Stanley George Bonney, Ware (GB)

(73) Assignee: Smithkline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/204,838

(22) PCT Filed: Feb. 21, 2001

(86) PCT No.: PCT/EP01/01942

§ 371 (c)(1),
(2), (4) Date: Aug. 23, 2002

(87) PCT Pub. No.: WO01/63368

PCT Pub. Date: Aug. 30, 2001

(65) Prior Publication Data

US 2003/0023337 A1 Jan. 30, 2003

(30) Foreign Application Priority Data

Feb. 26, 2000 (GB) .............................................. 0004455

(51) Int. Cl.⁷ ............................. G06F 7/00; G06F 19/00
(52) U.S. Cl. ....................... 700/116; 700/115; 700/225
(58) Field of Search ................................. 700/115, 116, 700/221, 225

(56) References Cited

U.S. PATENT DOCUMENTS

| | | | | | |
|---|---|---|---|---|---|
| 5,381,137 A | * | 1/1995 | Ghaem et al. | ........... | 340/572.5 |
| 5,469,363 A | * | 11/1995 | Saliga | ........... | 700/225 |
| 5,774,875 A | * | 6/1998 | Medeiros et al. | ........... | 705/28 |
| 5,831,859 A | * | 11/1998 | Medeiros et al. | ........... | 700/218 |
| 5,844,802 A | * | 12/1998 | Lepper et al. | ........... | 700/115 |
| 6,078,845 A | * | 6/2000 | Friedman | ........... | 700/104 |
| 6,366,824 B1 | * | 4/2002 | Nair et al. | ........... | 700/115 |
| 6,594,611 B2 | * | 7/2003 | Beffa | ........... | 702/119 |
| 2002/0198618 A1 | * | 12/2002 | Madden et al. | ........... | 700/101 |
| 2003/0064029 A1 | * | 4/2003 | Tarara et al. | ........... | 424/45 |

* cited by examiner

Primary Examiner—Leo Picard
Assistant Examiner—Elliot Frank
(74) Attorney, Agent, or Firm—James P. Riek

(57) ABSTRACT

There is provided a method for automatically tracking compliance in a manufacturing process involving successive manufacturing operations comprising selecting an object; associating an identifier with said object, said identifier comprising a memory; performing a first manufacturing operation relating to the object; following the successful completion of said first manufacturing operation, writing an associated compliance data item to the memory; performing one or more further manufacturing operations relating to the object; and following the successful completion of each said further manufacturing operation or any package thereof, writing an associated compliance data item to the memory.

54 Claims, 4 Drawing Sheets

COMPLIANCE TRACKING METHOD

The following is a U.S. National Phase filing under 35 USC 371 of PCT International Patent Application No. PCT/EP01/01942, filed 21 Feb. 2001, which claims priority to GB0004455.2, filed in the United Kingdom on 26 Feb. 2000.

TECHNICAL FIELD

The present invention relates to an automated method for checking compliance in a manufacturing method such as an assembly method.

BACKGROUND TO THE INVENTION

The manufacture of many products, particularly medical products requires careful quality control to ensure compliance with product specifications. It is common practice to mark the dispenser and any packaging therefor with various codings and serial numbers for use in checking final product integrity. Widely used marking techniques include printing and the use of bar codes.

There are two well-established methods of monitoring quality in a manufacturing method. The first which is often known as 'Quality Control' or 'QC' involves checking of the quality of a finished product against a defined set of compliance criteria and rejecting any finished products which do not meet all of the criteria. The second method, often referred to a 'Quality Assurance' or 'QA' involves making compliance checks at selected, successive stages in the manufacturing process and rejecting any product which fails to meet the criteria of any one check stage. The emphasis of the first method may thus be seen to be on monitoring the quality ('compliance') of the finished product and the emphasis of the second method on monitoring the quality ('compliance') of the various process steps in the manufacturing method.

It is desirable that the product itself or a support (e.g. a pallet or packaging) associated therewith bears some marking to show that each individual compliance check has been made and complied with. In a multi-stage 'QA' type process it may be appreciated to be inconvenient, complex and costly to successively mark the product using traditional printing and bar code methods. Furthermore, the final product will end up with many separate markings thereon which is undesirable from a product aesthetic standpoint.

The Applicants have now devised an improved method of checking compliance in a multi-stage manufacturing method. The method involves associating a memory with an object upon which successive manufacturing operations are to be performed. Following the successful completion of each successive manufacturing operation, a compliance data item is written to the memory. Following the completion of a pre-defined number of manufacturing operations the compliance data items are read from the memory and checked against a compliance data checklist to ensure that the pre-defined number of manufacturing operations has been successfully completed.

The memory can be configured to have a structure which allows for large amounts of discrete information to be stored thereon. Transfer of information to or from the memory is furthermore readily achievable by the use of a reader which is typically but not necessarily remote from the object, thereby miminising the need for direct product handling. In further aspects, the reader can be arranged to simultaneously read the memory of multiple tags on multiple objects.

A principal advantage of the present invention is the capability of the memory to store many items of compliance data which are written thereto at various defined points in the manufacturing method. The memory thereby provides a detailed and readily accessible product compliance history. Such product history information may, for example, be referred to in the event of a product recall. The compliance information could, for example, include data and time stamps. The memory might also be configured to include a unique serial number stored in encrypted form or in a password protectable part of the memory which uniquely identifies the product and therefore may assist in the detection and prevention of counterfeiting. The information could also include basic product information such as the nature of the product and usage information, customer information such as the name of the intended customer and distribution information such as the intended product destination.

SUMMARY OF INVENTION

According to one aspect of the present invention there is provided a method for automatically tracking compliance in a manufacturing process involving successive manufacturing operations comprising selecting an object; associating an identifier with said object, said identifier comprising a memory; performing a first manufacturing operation relating to the object; following the successful completion of said first manufacturing operation, writing an associated compliance data item to the memory; performing one or more further manufacturing operations relating to the object; and following the successful completion of each said further manufacturing operation or a package thereof, writing an associated compliance data item to the memory.

The term 'automatically' is used to mean non-manual, i.e. without manual intervention. In particular, the writing and/ or reading steps herein are conducted automatically.

Preferably, the method additionally comprises reading the memory prior to performing the first or any of the one or more manufacturing operations relating to the object.

Preferably, the memory comprises a unique signature data item and said reading step comprises reading said unique signature data item. More preferably, the unique signature data item is read only prior to performing the first manufacturing operation.

In one aspect, the unique signature data item has a unique number or code such as may be found on a bank note or traveller's cheque. In practical applications, it is anticipated that each identifier may be uniquely assigned a signature data item on manufacture, and that unique batches of signatures may be acquired from the manufacturer of the identifier under exclusive contract terms. The uniqueness of the identifier can assist in both product recall and counterfeiting aspects of the invention.

In a particular aspect, the unique signature data item is uniquely associated with a second unique data item which is stored on a distant datastore. Matching of the signature and second unique data items is through some secure matching process. For example, the signature data item may be read into a secure matching database comprising both matching tools and a database comprising a unique corresponding data item for each unique signature data item. Secure matching systems of this type are known and for example, described in United Kingdom Patent No. 2,252,270. Such systems are commonly used in 'pay as you go' phone cards for use with mobile phones.

The unique signature data item may comprise compliance data, but in most applications this will be stored as a separate compliance data item.

Preferably, the reading step comprises reading at least one compliance data item. More preferably, the method additionally comprises checking said at least one compliance data item against a defined compliance criterion. Most preferably, the at least one compliance data item is associated with the last performed manufacturing operation or any package thereof.

Two distinct variations of the compliance checking process can be envisaged.

In the first variation, the compliance data item comprises an operation or list of operations (possibly preloaded into the memory) which must be carried out for full compliance to be registered. The subsequent checking then involves 'ticking off' the compliance data item (by writing to the memory) associated with any operation once it has been completed. This variation is thus, a sort of 'tick the box' process.

In the second variation, a positive compliance data item for each manufacturing operation is written to the memory following the completion thereof. As the method progresses a positive listing of completed actions is written to the identifier. This variation is thus, a sort of 'completed actions listing' process.

Preferably, non-compliance with any check results in the abandonment of the manufacturing process for the object.

Preferably, the method additionally comprises a final reading step involving reading all compliance data items in the memory subsequent to the completion of all manufacturing operations. More preferably, the method additionally comprises checking said all compliance data items against defined full compliance criteria. Most preferably, compliance with said check results in writing of a full compliance data item (e.g. full product approval) to the memory.

The successive manufacturing operations may be performed as part of a single, continuous process at one location. Alternatively, the process may be split into separate parts with for example, an initial series of successive operations being performed at one site and a second or further series of successive operations being performed at second or further manufacturing sites. The sites may be under common, joint or different ownership; for example, the first part of the process might be a pre-assembly process conducted at a supplier's site, whereas the second part of the process, a full assembly process, is conducted at the primary manufacturer's site.

Preferably, a proportion of the manufacturing operations are carried out at a first manufacturing site and the remaining manufacturing operations are carried out at one or more further manufacturing sites distant from the first manufacturing site. In one aspect, the first manufacturing site and said one or more further manufacturing sites are linked via a network computer system, such as a secure intranet or enterprise resource planning network system, to enable transfer of data therebetween.

Preferably, the method comprises writing to the memory by wireless data transfer thereto. Preferably, the method comprises reading to the memory by wireless data transfer therefrom. Thus, the memory and any reader/writer therefore may be distantly located in non-wired relationship with each other. Any transfer of data is preferably in encrypted form.

In aspects, the wireless data transfer is by data transfer means selected from the group consisting of capacitative data transfer means, transformative coupling data transfer means, electrical data transfer means, magnetic data transfer means, optical data transfer means and radiofrequency data transfer means.

Capacitive data transfer involves the transfer of data from a writer to the identifier in the form of high energy alternating current, when the writer and identifier are in close proximity. These data are transferred to the memory for storage thereon. Similarly, data can be read from the memory when the identifier is in close proximity to an appropriate reader.

Transformer coupling data transfer involves transfer of data from the primary winding on a reader to a secondary winding on the identifier. The transformer supplies power to the identifier as well as information which can be written or read from the identifier with an appropriate writer/reader. Data are stored on the memory on the identifier.

An alternative form of electrical data transfer is by direct physical contact of, for example, two brushes, one of which contains an electrical signal. Power is supplied to the identifier to effect data transfer to write/read information from the memory using an appropriate writer/reader.

Magnetic data transfer is effected by the generation of a suitable magnetic field by, for example, inductive means. Energy is provided to effect data transfer to write/read information from the memory using a suitable writer/reader.

Data may also be transferred to/from the identifier by optical data transfer means. Visible or infra red light energy can be transmitted from a light emitting diode, acting as a writer, to a photo electric diode on the identifier. The photo electric diode can then translate the information contained in the signal into an electrical form which can be transferred and recorded on the memory. Information retrieval from the chip memory involves a light emitting diode on the identifier transmitting a signal back to a reader. A suitable standard method for two communication over an infrared link is "IrDA".

Data transfer may also be effected by radiofrequency data transfer means. Information is transmitted from a radiofrequency writer to an antenna on the identifier and transferred for storage to a memory. Data can be read from the chip by a suitable reader which transmits radiofrequency energy to the identifier, thereby energising the identifer to enable data transfer.

Suitably, the identifier additionally comprises an antenna for transmitting or receiving energy in e.g. optical, electrical or magnetic form.

In one aspect, the identifier is a radiofrequency identifier comprising an antenna for transmitting or receiving radiofrequency energy; and an integrated circuit chip connecting with said antenna, said chip comprising the memory.

The radiofrequency identifier can be any known radiofrequency identifier. Such identifiers are sometimes known as radiofrequency transponders or radiofrequency identification (RFID) tags. Suitable radiofrequency identifiers include those sold by Phillips Semiconductors of the Netherlands under the trade marks Hitag, and Icode those sold by Amtech Systems Corporation of the United States of America under the trade mark Intellitag, and those sold by Texas Instruments of the United States of America under the trade mark Tagit.

Preferably, the antenna of the radiofrequency identifier is capable of transmitting or receiving radiofrequency energy having a frequency of from 100 KHz to 2.5 GHz such as 125 KHz, 13.56 MHz or 2.4 GHz. Higher frequencies are preferred because the distance between the reader/writer and the identifier may be increased.

The RFID tags herein may be used in combination and/or integrated with other traditional product labelling methods including visual text, machine-readable text, bar codes and dot codes.

In one aspect, the radiofrequency identifier is connected to the object.

In another aspect, the object has a support associating therewith and the radiofrequency identifier connects to the support. Preferably, the support assists in transport of the object. More preferably, the support is a conveyor belt or pallet.

Where the radiofrequency identifier is connected to the conveyor belt, the object would remain associated with the identifier on the conveyor belt throughout one or more specific manufacturing processes. At the end of the process (or processes), once compliance data had been read from the radiofrequency identifier, the identifier would be dissociated from the object when it is removed from the conveyor belt. The memory on the identifier could then be reprogrammed for use with another object in the manufacturing process.

Where the radiofrequency identifier is connected to a pallet, the pallet may remain associated with the object throughout the manufacturing process (whether at one or more distinct manufacturing sites) even to the point of distribution, delivery and storage of the object prior to sales.

In one aspect, the manufacturing process is an assembly process. Preferably, the manufacturing process is a process for assembling a medical device. More preferably, the medical device is an inhalation device for use in the delivery of respiratory medicament.

In another aspect, the object is a container and the manufacturing process is a container filling process. Preferably, the container is an aerosol container and the filling process involves filling the aerosol container with a suspension of a medicament in a propellant. More preferably, said propellant comprises liquefied HFA134a, HFA-227 or carbon dioxide. More preferably, said aerosol container comprises a solution of a medicament in a solvent.

Alternatively, the container is a dry-powder container and the filling process involves filling the dry-powder container with medicament in dry-powder form. Preferably, said dry-powder container comprises a blister pack.

Other processes are envisaged herein including blending, coating, weighing, product testing and packaging processes.

Preferably, the medicament is selected from the group consisting of albuterol, salmeterol, fluticasone propionate, beclomethasone dipropionate, salts or solvates thereof and any mixtures thereof.

Preferably, the identifier is on a carrier suitable for mounting to the object or a support therefor. The carrier is preferably a flexible label, a rigid disc or a rectangular block, although other shapes and forms of carrier are envisaged.

Preferably, the carrier is mouldable to the object.

Preferably, the carrier encases the identifier. More preferably, the carrier forms a hermetic seal for the identifier.

Preferably, the carrier comprises an insulating material. More preferably, the insulating material comprises a glass material, a paper material or an organic polymeric material such as polypropylene.

Alternatively, the carrier comprises a ferrite material.

Preferably, the memory has plural memory areas thereon. The plural memory areas can be selected from a read only memory area, a write only memory area, a read/write memory area, a one time programmable memory area, a preset, non-amendable memory area and any mixtures thereof.

Preferably, any memory area contains data in encrypted form and/or is password protected.

Preferably, the reader is capable of reading multiple identifiers simultaneously by differentiating between individual identifiers within the same antenna field. The reader thus has 'anti-collision' capability.

In one aspect, the method additionally comprises transferring each compliance data item read from the memory to an (e.g. centralised) electronic data management system comprising a data memory for storage of data; a microprocessor for performing operations on said data; and a signal output for outputting a signal relating to the data or the outcome of an operation on the data. The electronic data management system may be connected to a networked computer system by any suitable method including a hard wired link or a wireless communications link such as one based on infra red or radiofrequency links.

In another aspect, the method additionally comprises transferring each compliance data item read from the memory to a distributed electronic data management system comprising plural electronic data collectors, each comprising a data memory for storage of data; a microprocessor for performing operations on said data; and a signal output for outputting a signal relating to the data or the outcome of an operation on the data, wherein said plural electronic data collectors are in network relationship to form said distributed electronic data management system.

In one aspect, the electronic data collectors may comprise what are known in the art as 'field devices' which are used for local data collection. Each 'field device' may be capable of wireless communication to the other or to the electronic data management system.

In one aspect, the electronic data management system forms part of a robotics system.

Preferably, the method additionally comprises communicating with a gateway to a network computer system to enable transfer of data between the network computer system and the electronic data management system. More preferably, the method enables two-way transfer of data between the network computer system and the electronic data management system.

The network computer system may comprise in embodiments, a local or wide area network, an intranet, an enterprise resource planning system or any similar network. Security features may be provided thereto including a firewall.

The communication (e.g. via a communicator) may be via radiofrequency or optical signals.

In one aspect, the communicator communicates directly with the gateway.

In another aspect, the communicator communicates with the gateway via a second communications device. Preferably, the second communications device is a telecommunications device, more preferably a cellular phone or pager. Preferably, the communicator communicates with the second communications device using radiofrequency signals. A suitable (e.g. spread spectrum) protocol is the Bluetooth (trade mark) standard which employs rapid (e.g. 1600 times a second) hopping between plural frequencies (e.g. 79 different frequencies). The protocol may further employ multiple sending of data bits (e.g. sending in triplicate) to reduce interference.

Preferably, the data is communicable between the network computer system and the electronic data management system in encrypted form. All suitable methods of encryption or partial encryption are envisaged. Password protection may also be employed.

In one aspect, the network computer system comprises a public access network computer system. The internet is one suitable example of a public access network computer system, wherein the gateway can be any suitable gateway thereto including gateways managed by an internet service provider. The public access network computer system may also form part of a telecommunications system, which may itself be either a traditional copper wire system, a cellular system or an optical network.

In another aspect, the network computer system comprises a private access network computer system and the gateway is a secure gateway. The private access network system may for example, comprise an intranet or extranet which may for example, be maintained by a health service provider or medicament manufacturer. The secure gateway may for example include password protection; a firewall; and suitable encryption means.

The method preferably comprises communicating with a user-specific network address in the network computer system. More preferably, the user-specific network address is selected from the group consisting of a web-site address, an e-mail address and a file transfer protocol address.

In another aspect of the present invention, there is provided a computer program comprising program means for, when executed on a computer, instructing the computer to control all of the steps of the method of the invention hereinbefore described.

In a further aspect of the present invention, there is provided a computer program product comprising a computer readable recording medium having recorded thereon a computer program comprising code means for, when executed on a computer, instructing said computer to control the steps in a method for automatically tracking compliance in a manufacturing process involving successive manufacturing operations of selecting an object;

associating an identifier with said object, said identifer comprising a memory;

performing a first manufacturing operation relating to the object;

following the successful completion of said first manufacturing operation, automatically writing an associated compliance data item to the memory;

performing one or more further manufacturing operations relating to the object; and following the successful completion of each said further manufacturing operation or any package thereof, writing an associated compliance data item to the memory.

BRIEF DESCRIPTION OF DRAWINGS

Embodiments of methods according to the invention will now be described with reference to the accompanying drawings in which.

DETAILED DESCRIPTION OF DRAWINGS

Figure 1:
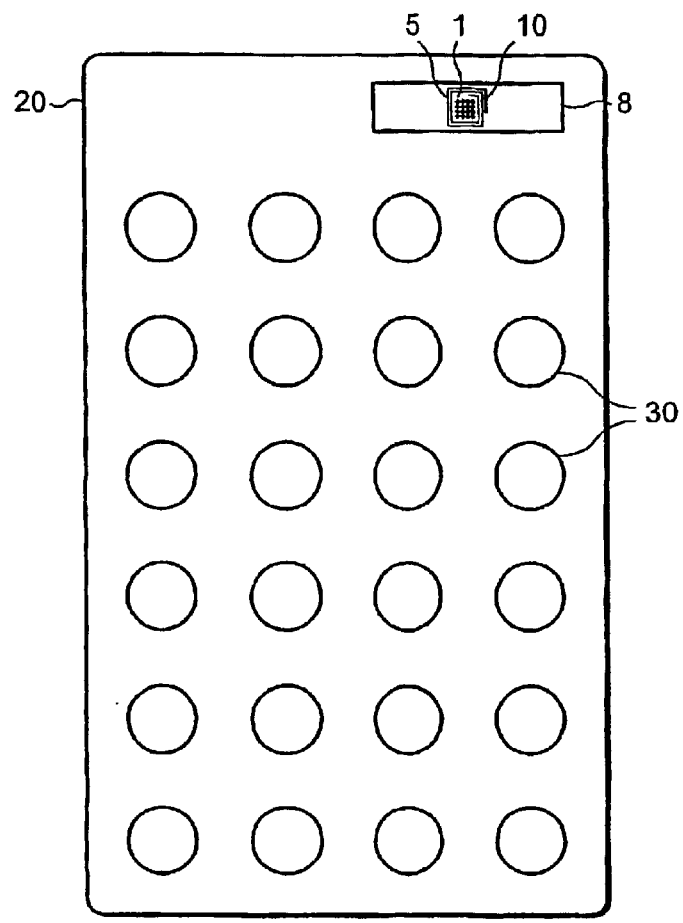
FIG. 1 is a plan view of an RFID tag attached to a blister pack.

FIG. 1 illustrates an RFID tag 10 attached to a blister pack 20 for packaging of medicaments. The RFID tag comprises an integrated circuit chip 1 connected to an antenna 5. The RFID tag illustrated is mounted on a rectangular carrier 8 composed of an insulating material such as a glass or ferrite material, to prevent electrical conductivity with any metallic foil (not shown) present in the blister pack.

In alternative embodiments, it will be understood that the carrier may take several different forms, such as a rectangular label as illustrated, a rectangular block or a circular disc. The carrier may be affixed to the object, for example the housing or aerosol container of a medicament dispenser, by adhesion, hermetic or welding means. Alternatively the tag may be directly moulded into the body of the object.

The pack contains a number of pockets 30 for storage of medicament. Once filled with medicament, blister packs are sealed, generally by heat treatment, to prevent ingress of moisture and/or microbial contamination.

Figure 2:
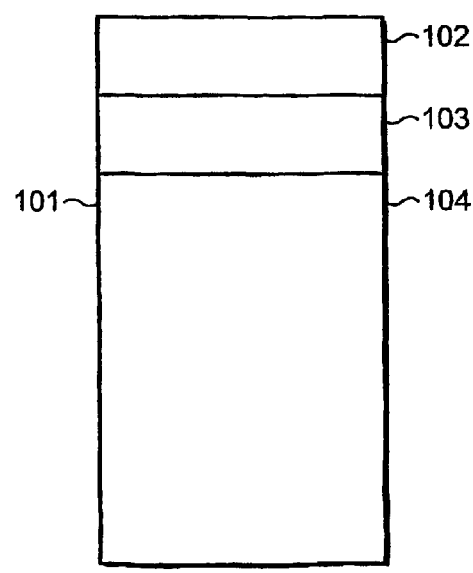
FIG. 2 is a schematic representation of the memory structure of an RFID tag.

FIG. 2 is a schematic representation of the memory structure of the RFID chip 101. Such tags are divided into unique blocks, typically numbering sixteen in total, with data being stored in non-volatile memory EEPROM, the EEPROM having a memory capacity of 512 bits with each block consisting of 4 bytes. However, for the sake of simplicity, in the illustration shown in FIG. 2 the tag is divided into three blocks 102–104 only.

The first block 102 contains unique tag identifiers such as serial numbers, this information being in a read only format and being encoded on the tag at the time of manufacture such that this information cannot be altered once set.

The second block 103 permits write access conditions to be determined for the third block 104, for example to allow read and write access to the remaining blocks. This block may be considered a 'secret area' in that access requires mutual authentication and enciphered data communications are used in this area. The second block 103 may be made read only once information has been written to it, i.e. it may become one time programmable.

The third block 104 can be considered to be a 'user' or 'public' area in that it may be programmed, by block two 103, such that information may be read from or written to it. This is generally the format in operation, information being read from and written to this area. Access can be password protected and data may be in encrypted format to enhance security.

In use, information from block one 102 (i.e. the unique serial number) will generally be used to identify the tag at each stage in a pre-determined process. Information will also be read from block three 104, to ensure that a given step in the operation has occurred. If satisfied that the operation has taken place successfully then additional information is written to block three 104, following the successful completion of the next stage in the process. Each step in the process is therefore validated and recorded by means of reading data on the chip and by transferring new information to it. These data can be stored electronically and the process monitored from a centralised data management system.

Figure 3:
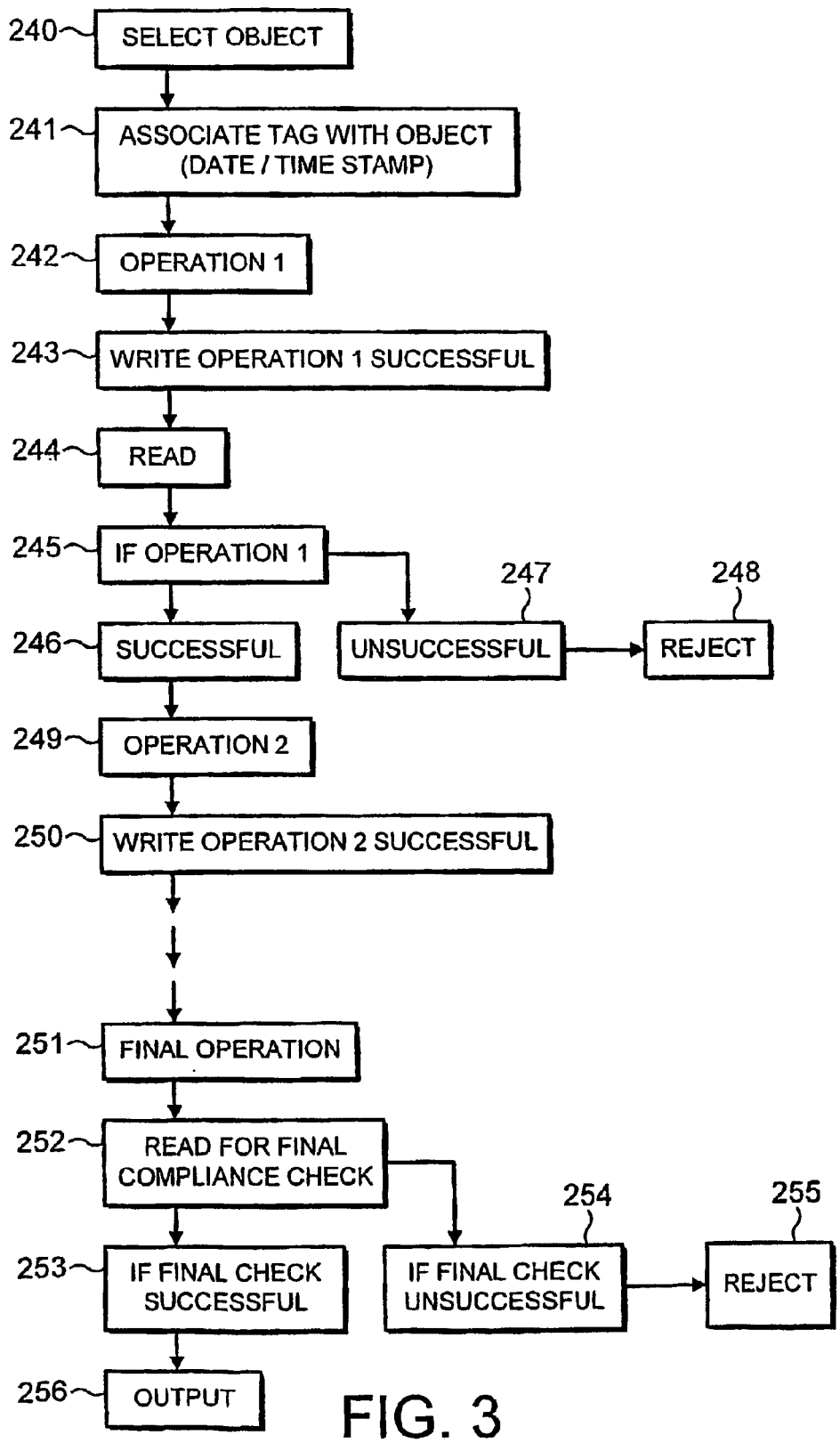
FIG. 3 is a flow diagram of a method for tracking compliance in a manufacturing process.

A flow diagram of a method for tracking compliance in a manufacturing process is shown in FIG. 3. The method begins by selecting the object 240 to be tagged with the RFID tag. An association between the object and the tag is made 241 and appropriate information, such as a date and time stamp, written to the tag chip. Operation 1 is then performed on the object 242 and, if completed successfully, data written to the chip 243. Before moving to the next operation the chip is read 244: if the chip does not contain a record of the previous task having been completed successfully 247 then the object is rejected 248; however, if this record is present 246 then a second operation 249 may be carried out on the object.

On completion of this second task information is written 250 to the chip and the object is prepared for the next operation. The chip is again read to ensure that an appropriate record is present before the system will permit the next operation to take place; the absence of such a record will result in the object being rejected at this stage.

This process of validating that an operation has been successfully conducted, by writing to and reading information from the chip in this manner, represents a series of 'gateways' or decision points through which objects must pass throughout the manufacturing process.

The method involves a final check for compliance at the end of all of the operations 251 whereby the reader will ensure that the chip contains records of each task having been carried out successfully 252. This represents a final decision point or gateway at which the object may be rejected 255 if the system is not satisfied 254 with the information present on the chip. However, if validation is successful 253, then the process is now complete and the object (still in association with its tag) will be considered a final product or output 256 from the process.

Figure 4:
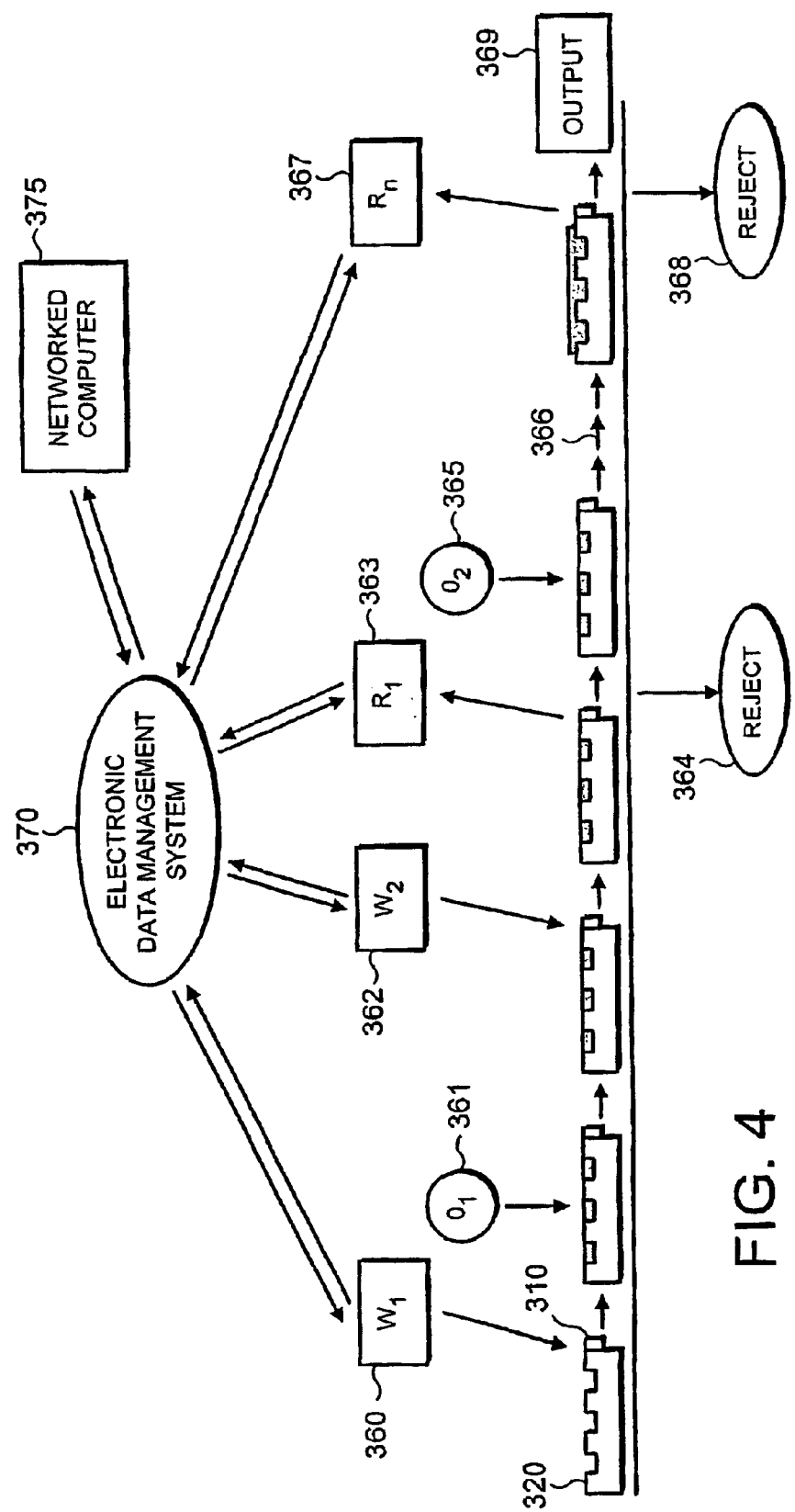
FIG. 4 is a schematic representation of a system employing a method for tracking compliance in a manufacturing process under the control of a centralised data management system.

A schematic representation of a system employing a method for tracking compliance in a manufacturing process is shown in FIG. 4. The diagram illustrates a simplified process for filling blister packs 320 with medicament and sealing the packs on addition of the drug.

An RFID tag 310 is associated with an empty blister pack 320. Data such as a date/time stamp is written 360 to the tag's chip. The first operation O1 is then carried out 361, such as filling the pockets of the pack with medicament. Information that this process has been successfully completed is written 362 to the chip by writer W2. This information is validated at 363 by reader R1; if the information is absent then the blister pack is rejected 364, if present then the next operation O2 is performed 365.

The process is repeated 366 at the same or different manufacturing sites which may, or may not, be distant from the first manufacturing site, until reader Rn validates 367 the entire process in a final compliance check. If the system is not satisfied that all of the operations have been successfully carried out then the blister pack is rejected 368. At any point of automation failure, the stage of each object in the process is known. However, if validation is successful then the process is complete and the blister pack is considered a final product or output 369.

In the diagram the process is controlled by an electronic data management system 370 which is capable of receiving and sending information to the chip readers R and writers W. This system may form part of a robotics system (not shown). The system may also be connected to a networked computer system 375 to allow transfer of data between both systems, preferably these data being in an encrypted format. The networked computer system may be a publicly accessible system, such as the internet, or a privately accessible system such as an intranet or extranet.

Figure 5:
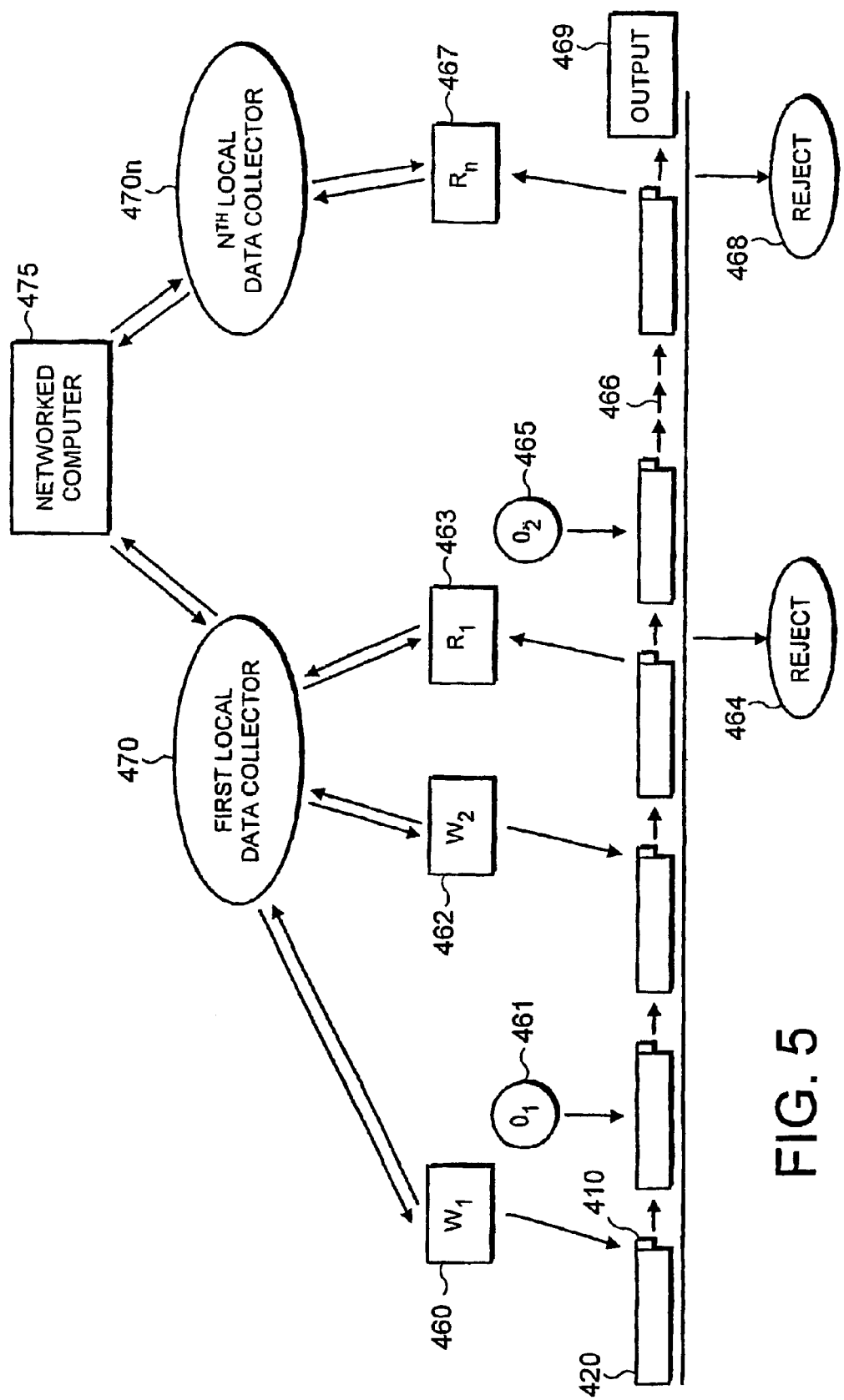
FIG. 5 is a schematic representation of a system employing a method for tracking compliance in a manufacturing process under the control of local data management collectors.

FIG. 5 depicts another system employing a method for tracking compliance in a manufacturing process which is controlled at a local, rather than centralised (as in FIG. 4), level. The diagram illustrates a schematic process involving a series of operations in the assembly of a product or output 469 from intermediate 420. The process may or may not be carried out at the same manufacturing site or at a series of manufacturing sites distant from each other.

RFID tag 410 may already have acceptance criteria pre-written on the tag at the point of tag manufacture, or these criteria may be written onto the tag prior to commencement of the assembly process. The tag 410 is first associated with the intermediate 420. Writer W1 writes data 460 (such as date/time stamp) to the tag 410 before the first operation O1 is initiated 461. Writer W2 writes 462 information that this operation has been completed to the tag 410. Reader R1 reads 463 and transfers these data, together with the acceptance criteria, from tag 410 to a local data collector 470. This system compares these data and either passes the intermediate 420 onto the next stage of assembly or rejects 464 it if the data do not match the acceptance criteria on the tag.

Second 465 operation O2 and successive 466 operations may then be performed on the intermediate 420, with data written to the tag 410 at each stage in the process. Acceptance/rejection 468 of the intermediate 420 continues to be determined locally by a series of local data management systems 470–470n which match data written to the tag 410 at each stage in the process against the pre-written acceptance criteria on the tag 410.

Each data collector 470–470n is networked as shown to allow transfer of data therebetween. The networked computer system may in embodiments form part of a publicly accessible system, such as the internet, or a privately accessible system such as an intranet or extranet.

The method of the invention is in one aspect suitable for manufacturing an inhalation device for dispensing medicament for the treatment of respiratory disorders such as disorders of the lungs and bronchial tracts including asthma and chronic obstructive pulmonary disorder (COPD).

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. as the sodium salt), ketotifen or nedocromil (e.g. as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6α, 9α-difluoro-11β-hydroxy-16α-methyl-3-oxo-17α-propionyloxy-androsta-1,4-diene-17β-carbothioic acid S-(2-oxo-tetrahydro-furan-3-yl) ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy) propyl] sulfonyl] ethyl] amino]ethyl-2(3H)-benzothiazolone; adenosine 2a agonists, e.g. 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate); α4 integrin inhibitors e.g. (2S)-3-[4-({[4-(aminocarbonyl)-1-piperidinyl] carbonyl}oxy)phenyl]-2-[((2S)-4-methyl-2-{[2-(2-methylphenoxy) acetyl] amino}pentanoyl)amino] propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament and/or to minimise the solubility of the medicament in the propellant. Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) or formoterol (e.g. as the fumarate salt) in combination with an anti-inflammatory steroid such as a beclomethasone ester (e.g., the dipropionate) or a fluticasone ester (e.g., the propionate) or budesonide. A particularly preferred combination is a combination of fluticasone propionate and salmeterol, or a salt thereof (particularly the xinafoate salt). A further combination of particular interest is budesonide and formoterol (e.g. as the fumarate salt).

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims.

What is claimed is:

1. A method for automatically tracking compliance in a manufacturing process involving successive manufacturing operations comprising
    selecting an object;
    associating an identifier with said object, said identifier comprising a memory, wherein the identifier is a radiofrequency identifier comprising an antenna for transmitting or receiving radiofrequency energy; and an integrated circuit chip, connecting with said antenna, said chip comprising the memory;
    performing a first manufacturing operation relating to the object;
    following the successful completion of said first manufacturing operation, writing an associated compliance data item to the memory;
    performing one or more further manufacturing operations relating to the object; and
    following the successful completion of said one or more further manufacturing operations, writing an associated compliance data item to the memory,
    wherein said object retains said identifier through distribution to consumers.

2. A method according to claim 1, additionally comprising reading the memory prior to performing the first or any of the one or more manufacturing operations relating to the object.

3. A method according to claim 2, wherein said memory comprises a unique signature data item and said reading step comprises reading said unique signature data item.

4. A method according to claim 3, wherein said unique signature data item is read only prior to performing the first manufacturing operation.

5. A method according to claim 2, wherein said reading step comprises reading at least one compliance data item.

6. A method according to claim 5, additionally comprising checking said at least one compliance data item against a defined compliance criterion.

7. A method according to claim 6, wherein at least one compliance data item is associated with the last performed manufacturing operation or a package thereof.

8. A method according to claim 6, wherein non-compliance with any check results in the abandonment of the manufacturing process for the object.

9. A method according to claim 2, wherein reading of the memory is by wireless data transfer therefrom.

10. A method according to claim 1, additionally comprising a final reading step involving reading all compliance data items in the memory subsequent to the completion of all manufacturing operations.

11. A method according to claim 10, additionally comprising checking said all compliance data items against defined full compliance criteria.

12. A method according to claim 11, wherein compliance with said check results in writing of a full compliance data item to the memory.

13. A method according to claim 1, wherein the first manufacturing operation is carried out at a first manufacturing site and at least one of the one or more further manufacturing operations is carried out at a second or further manufacturing site.

14. A method according to claim 13, wherein the fist manufacturing site and said one or more further manufacturing sites are linked via a network computer system to enable transfer of data therebetween.

15. A method according to claim 1, wherein writing to the memory is by wireless data transfer thereto.

16. A method according to claim 15, wherein said wireless data transfer is by data transfer means selected from the group consisting of capacitative data transfer means, transformative coupling data transfer means, electrical data transfer means and magnetic data transfer means.

17. A method according to claim 15, wherein said wireless data transfer is by optical data transfer means.

18. A method according to claim 15, wherein said wireless data transfer is by radiofrequency data transfer means.

19. A method according to claim 1, wherein the antenna is capable of transmitting or receiving radiofrequency energy having a frequency of from 100 KHz to 2.5 GHz.

20. A method according to claim 19, wherein the antenna is adapted to transmit or receive radiofrequency energy having a frequency selected from the group consisting of 125 KHz, 13.56 MHz and 2.4 GHz.

21. A method according to claim 1, wherein the identifier connects to the object.

22. A method according to claim 1, wherein the manufacturing process is an assembly process.

23. A method according to claim 22, wherein the manufacturing process is a process for assembling a medical device.

24. A method according to claim 23, wherein the medical device is an inhalation device.

25. A method according to claim 1, wherein the object is a container and the manufacturing process is a container filling process.

26. A method according to claim 25, wherein the container is an aerosol container and the filling process involves filling the aerosol container with a suspension of a medicament in a propellant.

27. A method according to claim 26, wherein, said propellant comprises liquefied HFA134a, HFA-227 or carbon dioxide.

28. A method according to claim 27, wherein said aerosol container comprises a solution of a medicament in a solvent.

29. A method according to claim 25, wherein the container is a dry-powder container and the filling process involves filling the dry-powder container with medicament in dry-powder form.

30. A method according to claim 29, wherein said dry-powder container comprises a blister pack.

31. A method according to claim 25, said filling process involves filling said container with a medicament and wherein the medicament is selected from the group consisting of albuterol, salmeterol, fluticasone propionate, beclomethasone dipropionate, salts or solvates thereof and any mixtures thereof.

32. A method according to claim 1, wherein the radiofrequency identifier is on a carrier suitable for mounting to the object or a support therefor.

33. A method according to claim 32, wherein the carrier is a flexible label.

34. A method according to claim 32, wherein the carrier is a rigid disc.

35. A method according to claim 32, wherein the carrier is a rectangular block.

36. A method according to claim 32, wherein the carrier is mouldable to the object.

37. A method according to claim 32, wherein the carrier encases the identifier.

38. A method according to claim 37, wherein the carrier forms a hermetic seal for the identifier.

39. A method according to claim 32, wherein the carrier comprises an insulating material.

40. A method according to claim 39, wherein the insulating material comprises a glass material, paper material or organic polymeric material.

41. A method according to claim 39, wherein the carrier comprises a ferrite material.

42. A method according to claim 1, wherein the memory is integrated memory having plural memory areas thereon.

43. A method according to claim 42, wherein any memory area contains data in encrypted form.

44. A method according to claim 1, additionally comprising transferring each compliance data item read from the memory to an electronic data management system comprising a data memory for storage of data;
a microprocessor for performing operations on said data; and
a signal output for outputting a signal relating to the data or the outcome of an operation on the data.

45. A method according to claim 44, wherein the electronic data management system forms part of a robotics system.

46. A method according to claim 44, additionally comprising communicating with a gateway to a network computer system to enable transfer of data between the network computer system and the electronic data management system or any individual electronic data collectors thereof.

47. A method according to claim 46, enabling two-way transfer of data between the network computer system and the electronic data management system.

48. A method according to claim 46, wherein the data are communicable between the network computer system and the electronic data management system in encrypted form.

49. A method according to claim 46, wherein the network computer system comprises a public access network computer system.

50. A method according to claim 46, wherein the network computer system comprises a private access network computer system and the gateway is a secure gateway.

51. A method according to claim 46, comprising communicating with a user-specific network address in the network computer system.

52. A method according to claim 51, wherein the user-specific network address is selected from the group consisting of a web-site address an e-mail address and a file transfer protocol address.

53. A method according to claim 1, additionally comprising transferring each compliance data item read from the memory to a distributed electronic data management system comprising plural electronic data collectors, each comprising a data memory for storage of data;
a microprocessor for performing operations on said data; and
a signal output for outputting a signal relating to the data or the outcome of an operation on the data,
wherein said plural electronic data collectors are in networked relationship to form said distributed electronic data management system.

54. A computer program product comprising a computer readable recording medium having recorded thereon a computer program comprising code means for, when executed on a computer, instructing said computer to control the steps in a method for automatically tracking compliance in a manufacturing process involving successive manufacturing operations of selecting an object;
associating an identifier with said object, said identifier comprising a memory, wherein the identifier is a radiofrequency identifier comprising an antenna for transmitting or receiving radiofrequency energy; and an integrated circuit chip connected with said antenna, said chip comprising the memory;
performing a first manufacturing operation relating to the object;
following the successful completion of said first manufacturing operation, automatically writing an associated compliance data item to the memory; performing one or more further manufacturing operations relating to the object; and
following the successful completion of said one or more further manufacturing operations, writing an associated compliance data item to the memory.
wherein said object retains said identifier through distribution to consumers.

* * * * *